United States Patent [19]

Hosick

[11] 4,120,976

[45] Oct. 17, 1978

[54] TREATMENTS FOR ARTHRITIS AND CAST DERMATITIS

[76] Inventor: Thomas A. Hosick, Box PMB 12-8, Atlanta, Ga. 30315

[21] Appl. No.: 860,126

[22] Filed: Dec. 13, 1977

[51] Int. Cl.² ............................................. A61K 31/36
[52] U.S. Cl. ..................................................... 424/282
[58] Field of Search ......................................... 424/282

[56] References Cited

U.S. PATENT DOCUMENTS

| 2,953,494 | 9/1960 | Cook et al. ............................ 424/282 |
| 2,974,148 | 3/1961 | Cook et al. ............................ 424/282 |

Primary Examiner—Stanley J. Friedman

[57] ABSTRACT

This invention relates to treatments for arthritis and cast dermatitis by the administration to patients of 3,4-methylenedioxyamphetamine and its non-toxic addition salts.

8 Claims, No Drawings

TREATMENTS FOR ARTHRITIS AND CAST DERMATITIS

BACKGROUND AND OBJECTIVES OF THE INVENTION

Arthritis is a series of degenerative diseases of the joints. Some of the diseases are of inflammatory etiology, such as rheumatoid arthritis and juvenile rheumatoid arthritis, and others are noninflammatory in nature, such as osteoarthritis. Two types of osteoarthritis are: (1) geriatric osteoarthritis (generally occurring in older persons), and (2) post-traumatic osteoarthritis (resulting from joint fractures and other injuries). Arthritis is characterized by pain and swelling of the joints, which may lead to increasing immobility thereof. The disease may finally lead to deformity and ankylosis, the fusing of the bones of the joint together through unnatural boney growth, permanently and totally immobilizing the joint with resulting crippling of the subject.

Millions of people throughout the world suffer daily with the pain and discomfort of arthritis and it is the world's leading crippling disease and can affect both young and old. The cause is unknown, but autoimmune mechanisms and virus infections have been postulated. Various therapeutic agents have been prescribed and administered by medical professionals in an effort to curb the effects of arthritis, such as aspirin, cortisone, adrenocorticotropic hormone (ACTH), gold salts, and indomethacin, but all have met with limited success.

With this background in mind, the present invention is presented and one of its objectives is to provide a better treatment for the effects of arthritis.

It is another objective of the present invention to provide a treatment for arthritis that may be administered orally or otherwise.

It is yet another object of the present invention to provide a method for relieving and reducing swelling of joints and other associated ailments following injuries thereto and to prevent or limit arthritis and cast dermatitis from occurring.

It is yet another objective of the present invention to provide a treatment for arthritic pain and swelling involving a therapeutic agent that is inexpensive to produce and can be manufactured with standard chemical equipment.

DESCRIPTION AND SUMMARY OF THE INVENTION

It has been determined that the administration of 3,4-methylenedioxyamphetamine (MDA) and its nontoxic acid addition salts, such as MDA hydrochloride (3,4-methylenedioxyamphetamine hydrochloride) will prevent and relieve swelling and pain which is associated with arthritis, for example, as may occur with joint fractures.

The treatment of patients can be performed either orally or by other means and the therapeutic effect of this compound will allow the victim of, for example, a broken ankle, to return to full use of the joint in relatively short time, while the pain, swelling, and problems with "cast dermatitis" are minimized during the bone healing process.

For example, an adult male may be administered 1.5 milligrams of MDA hydrochloride per kilogram of body weight immediately following reduction and casting of an ankle fracture. The same dose is continued at a rate of one dose every two or three days for approximately 12 weeks until the cast is removed, and may be continued beyond that time for whatever period is required following the injury for the patient to return to full use of the damaged ankle. The benefits received from the MDA hydrochloride treatment are: (1) the discomfort of the injury, especially that casued by "cast dermatitis" with its associated itching, is appreciably reduced; (2) the patient may return to full activities earlier than is ordinarily anticipated; (3) pain and swelling are less likely to be a significant problem during the healing process; and (4) post-traumatic osteoarthritis generally will not occur, or will be of significantly less severity. Since post-traumatic osteoarthritis can precipitate osteoarthritis of nontraumatic etiology in other joints, the significance of its prevention should be noted.

Free-base 3,4-methylenedioxyamphetamine may be prepared, for example, by the reduction of 3,4-methylenedioxy-beta-methyl-beta-nitrostyrene with lithium aluminum hydride in anhydrous ether, followed by the hydrolysis of the resulting adduct with cold dilute sulfuric acid, in which the MDA dissolves as its sulfate salt. The free base MDA is released by making the acid solution basic with concentrated potassium hydroxide solution and MDA is extracted into solvent ether.

If one desires to convert the free-base MDA to one of its salts, MDA need not be isolated from its ethereal solution, but the solution must be dried over potassium hydroxide pellets, followed by drying with anhydrous magnesium sulfate. To form the preferred embodiment of this invention, MDA hydrochloride, an anhydrous ether solution of free-base MDA just described is treated with an anhydrous ether solution of hydrogen chloride, preferably containing about 5 percent 1-propanol, until an equivalent amount of hydrogen chloride has been added. The resulting crystals of 3,4-methylenedioxyamphetamine hydrochloride are collected by filtration, such as on a Büchner suction funnel, and are recrystallized from boiling 1-propanol by the addition of anhydrous ether.

Two allotropic forms of crystalline 3,4-methylenedioxyamphetamine hydrochloride exist: the higher-melting "alpha" form and the lower-melting "beta" form. If MDA hydrochloride is generated in pure anhydrous ether, the alpha form is first received, then the beta form is generated after a transition period during which a sticky mixture of the two forms results. If the ether contains a small quantity of an alcohol such as 1-propanol, only the alpha form is obtained. Upon recrystallization as described above, only the alpha form is obtained.

As used herein, the term, MDA, refers to the dextro, levo, and racemic isomers of 3,4-methylenedioxyamphetamine. MDA salts as used herein refer to its nontoxic, pharmaceutically-acceptable salts, such as, for example, those salts derived from hydrochloric, hydrobromic, hydriodic, sulfuric, phosphoric, nitric, acetic, propionic, lactic, citric, tartaric, succinic, fumaric, maleic, malic, benzoic, salicylic, acetylsalicylic, acyrlic, cinnamic, 5,5-diethylbarbituric, sulfamic, ethanedisulfonic, p-toluenesulfonic, and like acids.

3,4-methylenedioxyamphetamine (MDA) may be prepared by the reduction of 3,4-methylenedioxy-beta-methyl-beta-nitrostyrene with lithium aluminum hydride, electrolysis, or with hydrogen in the presence of a palladium catalyst. 3,4-methylenedioxy-beta-methyl-beta-nitrostyrene in turn is prepared by the condensation of piperonal with nitroethane in the presence of a basic catalyst such as n-butylamine or sodium acetate.

The hydrochloride salt of MDA is prepared from the free base by neutralization with hydrogen chloride, preferably in an anhydrous solvent such as ether. The following procedure is an example of one synthesis of the preferred compound, MDA Hydrochloride, using 3,4-methylene-dioxy-beta-methyl-beta-nitrostyrene.

In a suitable container (such as a four-liter Erlenmeyer flask) 500 g. (3.33 moles) of piperonal are dissolved in 362.5 g. (3.5 moles) of nitroethane, using a little heat, if necessary, to aid in dissolution. The solution is cooled to room temperature and 30 ml. of n-butylamine are added. The solution is then placed in the dark and allowed to stand at room temperature for approximately two weeks. At that time crystallization will have occurred. Thereafter the crystals are dissolved in a minimal amount of boiling methanol and the solution is then allowed to cool for approximately six hours with occasional swirling. Yellow crystals will have formed which can be collected on a large Buchner suction funnel, and are washed with a little cold methanol, and are allowed to dry. The yield should be approximately 500 grams of 3,4-methylene-dioxy-beta-methyl-beta-nitrostyrene.

To form 3,4-methylenedioxyamphetamine from the 3,4-methylene-dioxy-beta-methyl-beta-nitrostyrene, the following procedure is utilized: In a six-liter Erlenmeyer flask, the bottom is covered with about ¾ of an inch of anhydrous ethyl ether and 25.5 g. (0.67 moles) of freshly ground lithium aluminum hydride are carefully added. Another solution is prepared by dissolving 64.2 g. (0.31 mole) of 3,4-methylene-dioxy-beta-methyl-beta-nitrostyrene in 3000 ml. of anhydrous ether in a four-liter Erlenmeyer flask (heat may be added to aid in dissolving, if necessary). The latter solution is slowly added to the contents of the six-liter flask as such a rate that ether vapor evolution does not blow the incoming stream of liquid out of the neck of the flask. If desired, one may modify the described apparatus to include a high-capacity condenser to recover ether vapor. After addition of the latter solution is complete, the reaction mixture is maintained at about 30° C. for 30 minutes or at reflux for 30 minutes, if a reflux condenser is utilized.

To hydrolize the resulting adduct, one conventional household ice cube is added and the solution is swirled until the vigorous reaction ceases. This process is repeated one ice cube at a time until further additions of ice cause no further vigorous reaction. Next, about 200 ml. of a mixture of crushed ice and water are added carefully with swirling. A solution of chilled sulfuric acid is made by pouring 100 ml. of concentrated sulfuric acid (with caution) into a two-liter beaker full of crushed ice (no water). While swirling, the diluted sulfuric acid is carefully added to the reaction mixture in the six-liter flask. After addition is complete, the contents are transferred to a six-liter separatory funnel and are shaken carefully, allowed to separate, and the lower aqueous acid layer containing the MDA sulfate salt is drawn off. The ether layer may be saved to reclaim the ether.

A concentrated solution of potassium hydroxide (KOH), is added to the acid/sulfate salt layer just to make it basic to wide-range pH paper. A like quantity of the KOH solution is added to convert the precipitated aluminum hydroxide to the more-soluble potassium aluminate. This basic solution containing MDA is extracted, after cooling, with three 300-ml. portions of U.S.P. ether, using the six-liter separatory funnel and by adding enough additional water so that only shaking room is left in the funnel. Often separation of the two layers is difficult, and the layer interface may be vacuum-filtered to obtain complete separation. The upper ether extract layer containing liquid free-base 3,4-methylenedioxyamphetamine, is dried over 85% KOH pellets for 30 minutes with occasional swirling. If the ethereal solution should become cloudy, it is decanted into a fresh dry flask and treated with anhydrous magnesium sulfate for further drying. After removal of the drying agent via filtration, the dried ethereal solution of free-base MDA is ready for conversion into its hydrochloride salt without further isolation.

For hydrochloride salt conversion of the free-base MDA, a solution of dry hydrogen chloride in anhydrous ether is prepared by drying a suspension of concentrated hydrochloric acid in anhydrous ether first over an ample quantity of anhydrous 4 or 8 mesh calcium chloride for 30 minutes, filtering out the hydrated calcium chloride by gravity filtration, and then treating the solution with anhydrous magnesium sulfate for at least one hour. Just before use, the latter drying solution is gravity filtered and enough pure 1-propanol is added to bring the solution to about 5 percent in respect to 1-propanol (5% propanol). This solution is then used to titrate the anhydrous ether solution of free-base MDA to a pH of 7 (using wide range pH paper). A pH of 7 is just shy of the true endpoint. The titration results in the immediate crystallization of the desired product, 3,4-methylenedioxyamphetamine hydrochloride, which is collected on a Buchner suction funnel and is washed with anhydrous ether and is dried by continuous vacuum.

A yield of at least 32 grams of product (MDA Hydrochloride) in excess of 99% purity should be obtained by this method. If desired, the salt may be recrystallized by dissolving it in a minimal quantity of boiling 1-proponal, followed by addition of anhydrous ether until the solution is barely cloudy. The solution is then cooled in a refrigerator for crystallization and the crystals are collected as before. A few more crystals may be obtained by addition of more of the ether-hydrogen chloride solution to the mother liquor from which the first crystals came.

MDA or its salts may be employed with any suitable pharmaceutical carrier, either a solid or a liquid for administration purposes. Exemplary of solid carriers are talc, corn starch, dextrose, lactose, mannitol, inositol, ethyl cellulose, magnesium stearate, stearic acid, agar, pectin, gelatin, and anacia. Examples of liquid carriers are water, olive oil, peanut oil, and sesame oil.

A variety of pharmaceutical forms can be employed, such as tablets, capsules, enterically coated pills, or others. Salts of MDA may also be employed in liquid solution form for injection and the liquid free-base MDA can be employed for use in an inhaler and may be employed with subsidiary medications such as menthol, camphor, methyl salicylate, and similar substances.

The per dosage form may consist, for example for oral doses, of a tablet formed of 50 milligrams of the hydrochloride salt of MDA in rates of 0.2 to 1.5 milligrams per kilogram of body weight approximately every 6 hours as needed with an admixture, for example, of talc and stearic acid as a lubricant and with a suitable binder such as lactose. When properly mixed, these ingredients can be combined into tablets, pellets, or capsules as desired.

As another example of the useful benefits of administering MDA or its addition salts, an elderly patient afflicted with arthritis in the left ankle may be unable to walk adequately without suffering severe pain. Such a patient could be prescribed MDA tablets of sufficient strength for daily, bidaily, or tridaily dosages as required to reduce the pain and thus allow normal or improved use of the ankle.

A maintenance schedule could be established by the patient's physician and periodic check-ups would provide proper safeguards for the patient.

Although 3,4-methylenedioxyamphetamine is related in chemical structure to the amphetamine drugs and is a CNS stimulant, it does not have the sympathomimetic properties of the amphetamine drugs such as amphetamine and N-methylamphetamine.

Various other derivatives of MDA and its salts can be conceived by those skilled in the art and the examples shown herein are not for the purpose of limiting the scope of the invention.

I claim:

1. A method for the treatment of arthritis comprising administering to arthritics for the relief of symptoms accompanying arthritis a member selected from the group consisting of 3,4-methylenedioxyamphetamine and its non-toxic acid addition salts in dosage amounts of approximately 0.2 to 1.5 milligrams per kilogram of body weight.

2. A method for the treatment of arthritis as claimed in claim 1, wherein the administration is performed every six hours.

3. A method for the treatment of arthritis as claimed in claim 1, in which the member selected comprises 3,4-methylenedioxyamphetamine hydrochloride.

4. A method for the treatment of arthritis as claimed in claim 1, wherein said administration is oral.

5. A method for the treatment of arthritis as claimed in claim 1, wherein said group member is combined with a suitable carrier.

6. A method for the treatment of symptoms accompanying cast dermatitis of those afflicted comprising administering to the afflicted approximately 1.5 milligrams of a member selected from a group consisting of 3,4-methylenedioxyamphetamine and its non-toxic acid addition salts per kilogram of body weight.

7. A method for the treatment of symptoms accompanying cast dermatitis as claimed in claim 6, wherein the administration is performed every two-three days.

8. A method for the treatment of symptoms accompanying cast dermatitis as claimed in claim 6, in which the member selected comprises 3,4-methylenedioxyamphetamine hydrochloride.

* * * * *

UNITED STATES PATENT OFFICE
CERTIFICATE OF CORRECTION

Patent No. 4,120,976                    Dated October 17, 1978

Inventor(s) Thomas A. Hosick

It is certified that error appears in the above-identified patent and that said Letters Patent are hereby corrected as shown below:

On the title page, the inventor's address should read -- Thomas A. Hosick
    c/o Mr. S. Ford Thomas
    811 Park Street
    Bowling Green, Ken. 42101 --.

Column 2, line 58, "acyrlic" should read -- acrylic --.

Column 2, line 61, "3,4-methylenedioxyamphetamine" should read -- 3,4-Methylenedioxyamphetamine --.

Column 3, line 35, "as" should read -- at --.

Column 4, line 30, "Buchner" should read -- Büchner --.

Column 4, line 49, "anacia" should read -- acacia --.

Signed and Sealed this

Eighth Day of May 1979

[SEAL]

Attest:

RUTH C. MASON
Attesting Officer

DONALD W. BANNER
Commissioner of Patents and Trademarks